United States Patent [19]

Harris

[11] Patent Number: 4,473,094

[45] Date of Patent: Sep. 25, 1984

[54] AIR INLET

[75] Inventor: Christopher Harris, Redditch, England

[73] Assignee: Anchor Continental Incorporated, Columbia, S.C.

[21] Appl. No.: 386,776

[22] Filed: Jun. 9, 1982

[30] Foreign Application Priority Data

Jun. 12, 1981 [GB] United Kingdom ............... 8118161

[51] Int. Cl.³ .................. F16K 24/00; F16K 15/14
[52] U.S. Cl. .................................. 137/588; 137/846; 137/850; 137/550; 604/405; 604/441
[58] Field of Search ................... 137/846–850, 137/550, 588; 604/405, 411

[56] References Cited

U.S. PATENT DOCUMENTS

| 2,986,098 | 5/1961 | Trout et al. | 137/850 |
| 3,157,481 | 11/1964 | Bujon | 285/260 |
| 3,527,029 | 9/1970 | Kirschner | 604/405 |
| 3,662,752 | 5/1972 | Yokoyoma | 604/405 |
| 3,710,942 | 1/1973 | Rosenberg | 137/846 |
| 3,780,943 | 12/1973 | Lilja | 137/846 |
| 3,783,895 | 1/1974 | Weichselbaum | 604/411 |
| 3,797,521 | 3/1974 | King | 137/533.11 |
| 3,886,937 | 6/1975 | Bobo et al. | 137/850 |
| 4,192,919 | 3/1980 | Raghavachari | 604/405 |

Primary Examiner—A. Michael Chambers
Attorney, Agent, or Firm—F. R. Brockington

[57] ABSTRACT

An integral air inlet which in use admits filtered gases into a fluid container, especially infusion fluid containers, comprises a needle sealed to a housing which is closed by an air filter, the housing having disposed within it a duck bill valve which permits gas to flow from the outside and into the fluid container. The presence of the duck bill valve prevents fluid contacting the air filter thereby reducing the risk of bacterial contamination the fluid when gas is admitted.

8 Claims, 4 Drawing Figures

AIR INLET

This invention relates to air inlets for use with infusion fluid containers.

Fluid containers adapted for administration of fluids by infusion are commonly manufactured of glass or other rigid material. Such containers have as an outlet a neck portion sealed by a rubber or plastic membrane. Normally in use the container is suspended vertically with the neck pointing downwards. The fluid is drawn off from the container by piercing the membrane of the outlet with a sharp hollow needle which is in turn coupled to a tube leading to a fluid administration device, connected in turn to an intravenous access device. If the container is of glass or other rigid material an additional means must be provided to admit air to the container to replace the fluid as it is drawn off and thereby enable a steady continuous flow of fluid to be maintained to the recipient. Clearly it is desirable that the air should be filtered before entering the fluid container to avoid contaminating the fluid with bacteria, dust and other deleterious material, but especially bacteria.

Suitable air filter assemblies are described in U.S. Pat. No. 3,157,481. In one embodiment the assembly comprises a piercing cannula sealed to a tubular body carrying an air filter. When in use the cannula is pushed through the membrane in the neck of the fluid container. A second embodiment comprised a fluid container having a second neck onto which is sealed an air filter. Both these embodiments by omitting a one-way valve allow the infusion fluid to contact the air-filter which necessitates efficient sealing of the air-filter to the tubular body to avoid the possibility of contamination and leakage of the fluid. A third embodiment shows an assembly having a one-way ball valve in a second neck in the fluid container which carries an air filter. The ball must be free of scratches or other imperfections to avoid fluid leaking past the ball and being contaminated and then re-admitted to the fluid container when the valve opens to admit air. A second assembly containing an improved ball-valve system is described in U.S. Pat. No. 3,797,521. However this patent is concerned with a dispensing closure in which the breather tube and outflow tube are combined into one piercing device. This type of device is complex and may be difficult to manufacture and further tends to admit air adjacent to the fluid exit point which may cause air bubbles to be sucked back into the administration device as the fluid leaves the container.

The present invention provides a simple, easy to produce device for admitting air or other gases to a fluid container which helps to mitigate the disadvantages described above particularly in preventing fluid contacting the air filter thereby providing a means by which bacteria may be admitted to the fluid container.

Accordingly the present invention provides an integral air inlet comprising a needle sealed to a housing which is closed by an air filter characterised in that disposed within the housing is a duck bill valve which permits gas to flow from the outside and leave through the needle.

Suitably the duck bill valve is made of a soft elastomeric material for example rubber.

Suitably the duck bill valve has a circular cross-section perpendicular to the direction of the flow of the gas tapering at one end to form a portion in the shape of a duck bill and at the other end a flange which is of greater diameter than the duck bill portion of the valve. In a second suitable form of the duck bill valve a cylindrical portion separates the duck bill portion from the flange. The shape of the preferred valves is shown in FIGS. 1 and 3 as in hereafter described. Suitable valves are available from Vernay Laboratories Inc. Yellow Springs, Ohio, U.S.A.

The advantages of using a valve of the duck bill type include (a) the valve prevents any contact between the administration fluid and the filter assembly thereby reducing further the risk of contamination of the fluid by air entering the container via the inlet and (b) the valve protects the filter membrane from adverse pressure changes which may distort or damage the membrane endangering its integrity.

Suitably the housing for use in the present invention has an internal longitudinal bore having at least two sections of different diameters. In a preferred form there are two such sections. A shoulder is formed at the point at which the two sections meet. The internal diameter of the bore in the centre of the housing being smaller than that of the second section of the bore. The diameters of the respective sections of bore will be such that the duck bill portion of the valve will be held without distortion in the section of bore with the smaller diameter whilst the flange of the valve will rest against the shoulder between the two sections of bore. In the second suitable form of the valve the cylindrical portion of the valve will form an interference fit with the internal surface of the smaller bore.

The housing may be manufactured by injection moulding of a polymeric material. Suitably the polymeric material is a thermoplastic polymer, for example polyethylene, polypropylene, polyvinyl chloride or nylon. A preferred thermoplastic polymer is rigid polyvinyl chloride. The housing is generally circular in cross-section and optionally finger grips or ribs will be present on at least part of the external surface of the housing to aid handling and insertion of the device.

Suitable the air filter for use in the present invention is a cylinder of polymeric material having at one end a filter means. Suitably the air filter is moulded from a thermoplastic material. Preferably the thermoplastic material is polyethylene. The diameter of the air filter will be such that when inserted in the larger bore of the housing it will form an interference fit with the internal surface of the bore. The length of the air filter will be such that it will compress the flange of the duck bill flange against the housing to form a fluid tight seal.

Aptly the filter means comprises a membrane filter supported by a woven matrix. Suitably the filter means comprises a membrane filter supported by a woven matrix. Suitably the membrane filter is of a hydrophobic polymeric material having a pore size that will screen and prevent the passage of microorganisms. Suitable hydrophobic polymeric materials include hydrophobic cellulose esters, polyvinyl chloride-acrylonitrile copolymer or polytetrafluoroethylene. Suitably the woven matrix is of nylon or glass fibre. The woven matrix supports the membrane filter against abrupt changes in pressure between the inside and outside of the fluid container. Air filters suitable for use in this invention are available form Filtertek Inc., Hebron, Illinois, U.S.A.

The needle for use in the present invention is suitably made from metal and is preferably made of stainless steel. The length of the needle will be such as to pierce the membrane of the fluid container and remain above any administration device or spike inserted into the same membrane thereby reducing the risk of any gas bubbles entering the fluid container via the needle being drawn across to the outlet point and being sucked into the administration device to cause occlusion of the flow or damage to the recipient of the fluid. Suitably the length of the needle is 30 to 70 mm and preferably 45 to 65 mm. The needle is ground to a sharp point at one end and the other end cut square and is sealed into the housing. The needle may be sealed to the housing by interference fit, force fit, bonding, induction welding or insert moulding.

Aptly the needle is covered by a protector. Suitably the protector is a tube of extruded thermoplastic polymer, for example polyethylene, polypropylene or polyvinylchloride which will be cut to sufficient length to cover the hollow needle to prevent damage or contamination while being readied for use. The protector will have an internal diameter such that it will fit onto the housing and be held in place by an interference fit.

From the foregoing it is clear that in a preferred embodiment the present invention comprises essentially of a needle sealed to a housing which is closed by an air filter characterised in that housing has a longitudinal bore of two different internal diameters having a shoulder at the point at which they meet such that the duck bill valve is held within the smaller bore its flange placed against the shoulder and is held in compression against the shoulder by the air filter to give an air-tight, fluid-tight seal.

In a second preferred embodiment the present invention comprises essentially of a needle sealed to a housing which is closed by an air filter characterised in that the housing has a longitudinal bore of two different internal diameters having a shoulder at the point at which they meet such that the duck bill valve is held within the smaller bore its cylindrical portion forming an air-tight fluid-tight seal against the internal surface of the smaller bore and its flange placed against the shoulder.

In either embodiment the needle may be covered by a protector.

The air inlet may be manufactured by the steps of (i) sealing the needle into the housing (ii) inserting the duck bill valve in its correct position (iii) inserting the air filter into the housing. These steps may be performed manually or automatically. Finally the needle protector is fitted and the assembled air inlet sealed in packaging. The packaging and its contents are then sterilised. Suitably sterilisation is carried out using ethylene oxide gas.

A further embodiment of the invention comprises a sterile air inlet of any of the embodiments described above.

A preferred embodiment of the present invention is described with reference to the following drawings.

Figure 1:
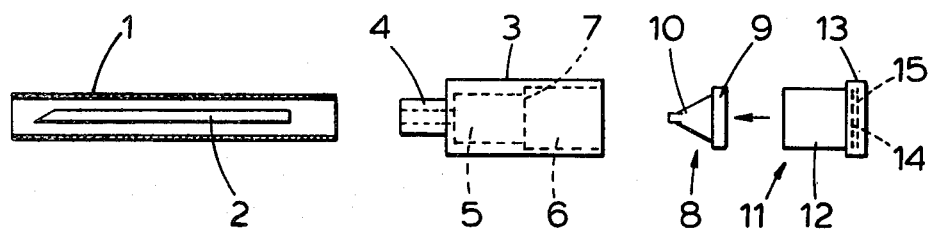
FIG. 1 is an exploded view of the component parts of the air inlet and needle protector.
Figure 2:
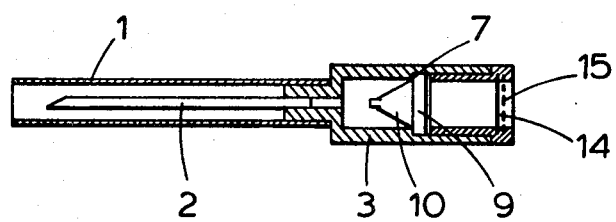
FIG. 2 is a cross-section of an assembled air inlet with the needle protector in place.

In FIG. 1 the component parts of the air inlet are the open tip protector (1) which protects the hollow needle (2) from contamination or damage on removal from the packing prior to use. The protector has an internal diameter such that it is held by an interference fit on the narrower part (4) of the housing (3), as shown in FIG. 2. The needle (2) has a sharpened end for piercing the membrane of the fluid container and a squared end which is bonded into the housing (3). In the wider part of the housing (4) the bore is of two different diameters thereby defining internal spaces (5) and (6) and between them an internal shoulder (7). The duck bill valve (8) is of a size that when in the housing (3) the flange (9) rests against the shoulder (7) and the body of the valve (10) is held in space (5) without being compressed or distorted. The valve permits the passage of air or other fluid in the direction of the arrow whilst preventing flow in the reverse direction. The air filter (11) comprises a moulded tube (12) a flange (13) filter membrane (14) and filter support (15). The diameter and dimensions of the tube (12) are such as to form an interference fit with the body housing and to seal the valve flange (9) against the shoulder (7) by compression. The filter membrane (14) will permit passage of air or other gases but not bacteria. The woven fabric support (15) prevents rupture of the membrane by any inrush of air. The assembled air inlet is shown in FIG. 2.

Figure 3:
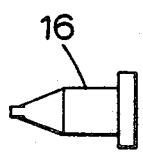
FIG. 3 is a representation of an alternative duck bill one-way valve which may be used in the air inlet.

FIG. 3 shows an alternative form of duck-billed valve. The external radius of the parallel portion (16) being chosen to form an interference fit with the body housing (3) within the space (5) so that the inlet is sealed without the filter assembly being used to compress the flange against the shoulder.

Figure 4:
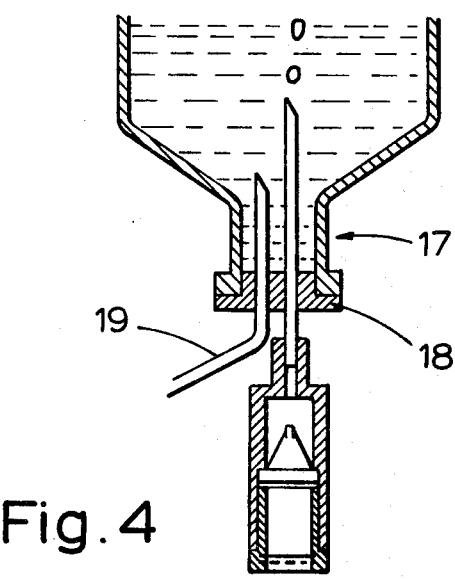
FIG. 4 is a representation of the air inlet in position in the outlet of a fluid container.

FIG. 4 shows the air inlet in position in a fluid container out-let (17) having pierced the membrane (18) which has also been pierced by a cannula (19) leading to an administration device (not shown). The length of the needle (2) is such that the bubbles enter the fluid away from the cannula (19).

From forgoing it is clear that the present invention provides an integral air inlet for use with a fluid container which in use prevents admission of bacteria into the interior of the container comprising a needle sealed into a housing which is closed by an air filter characterised in that disposal with the housing is a duck bill valve which permits gas to flow from the outside and leave through the needle.

Preferred duck bill valves are valves which comprise a flange portion and a pair of duck bill lips which are angled towards each other to meet and form a normally closed valve. Optionally the flange portion and duck bill portion may be separated by a cylindrical portion. Such valves will allow fluid to pass in one direction only.

EXAMPLE 1

An air inlet comprises a needle protector, a needle having a pointed end and a square end, a housing, a duck bill valve and an air filter. The air inlet is assembled automatically by grasping the needle firmly, placing the valve inside the housing, inserting the filter means in the end of the housing and finally pushing the housing assembly onto the square end of the needle whereby the valve and filter means are pushed onto the housing and the needle pushed onto the housing to form a secure fit. The needle protector is placed over the needle.

The assembled air inlet may be sealed into a suitable shaped package and sterilised using ethylene oxide gas.

In use the air inlet is removed from its package and the needle protector removed. The sharp end of the needle is pushed through the membrane in the neck of the fluid container, thus filtered air is admitted to the fluid container as fluid is removed.

What I claim is:

1. An integral air inlet for use with a container which dispenses a liquid and which in use prevents admission of bacteria into the interior of the container which integral air inlet comprises a housing; a needle sealed into the forward end of the housing; an air filter which closes the rearward end of the housing; and a duck bill valve of soft elastomeric material disposed within the housing rearward of the needle but forward of the air filter, which housing has a longitudinal bore of two different internal diameters having a shoulder at the point at which the two bores meet and which duck bill valve comprises a valve portion and a flange portion whereby the valve portion is disposed within the small bore of the housing and the flange portion is in the larger bore and is held against the shoulder in compression by the air filter to give an air-tight, fluid tight seal between the housing and the flange and whereby the valve operates to allow air to flow from the outside of the inlet and leave through the needle but prevents liquid from the container wetting the air filter.

2. An integral air inlet as claimed in claim 1 in which the needle is formed from stainless steel and is from 30 to 70 mm in length whereby when operable in a container the end of the needle will be above the liquid outlet and prevent air bubbles entering the container being drawn into the liquid outlet.

3. An integral air inlet as claimed in claim 1 in which the air filter contains a filter means comprising a hydrophobic membrane filter supported by a woven matrix.

4. An integral air inlet as claimed in claim 1 in which the air inlet is sterile and is in a sealed package.

5. An integral air inlet for use with a container which dispenses a liquid and which in use prevents admission of bacteria into the interior of the container which integral air inlet comprises a housing; a needle sealed into the forward end of the housing; an air filter which closes the rearward end of the housing; and a duck bill valve of soft elastomeric material disposed within the housing rearward of the needle but forward of the air filter, which housing has a longitudinal bore of two different internal diameters having a shoulder at the point at which the two bores meet and which duck bill valve comprises a cylindrical valve portion and a flange portion whereby the cylindrical valve portion is disposed within the smaller bore to form an air-tight, fluid-tight seal against the internal surface of the smaller bore and the flange portion is in the larger bore and is held against the shoulder in compression by the air filter and whereby the valve operates to allow air to flow from the outside of the inlet and leave through the needle but prevents liquid from the container wetting the air filter.

6. An integral air inlet as claimed in claim 5 in which the needle is formed from stainless steel and is from 30 to 70 mm in length whereby when operable in a container the end of the needle will be above the liquid outlet and prevent air bubbles entering the container being drawn into the liquid outlet.

7. An integral air inlet as claimed in claim 5 in which the air filter contains a filter means comprising a hydrophobic membrane filter supported by a woven matrix.

8. An integral air inlet as claimed in claim 5 in which the air inlet is sterile and is in a sealed package.

* * * * *